US010918351B2

(12) United States Patent
Muraoka (10) Patent No.: US 10,918,351 B2
(45) Date of Patent: Feb. 16, 2021

(54) RADIOGRAPHIC-IMAGE PROCESSING APPARATUS

(71) Applicant: KONICA MINOLTA, INC., Chiyoda-ku (JP)

(72) Inventor: Shintaro Muraoka, Hachioji (JP)

(73) Assignee: KONICA MINOLTA, INC., Tokyo (JP)

(*) Notice: Subject to any disclaimer, the term of this patent is extended or adjusted under 35 U.S.C. 154(b) by 73 days.

(21) Appl. No.: 15/676,002

(22) Filed: Aug. 14, 2017

(65) Prior Publication Data

US 2018/0049712 A1 Feb. 22, 2018

(30) Foreign Application Priority Data

Aug. 19, 2016 (JP) .............................. JP2016-160944

(51) Int. Cl.
*A61B 6/00* (2006.01)
*G06T 7/00* (2017.01)

(52) U.S. Cl.
CPC .............. *A61B 6/5217* (2013.01); *A61B 6/50* (2013.01); *G06T 7/0016* (2013.01); *A61B 6/4405* (2013.01); *G06T 2207/10116* (2013.01); *G06T 2207/30061* (2013.01)

(58) Field of Classification Search
CPC ...... A61B 6/463; G06T 7/0012; G06F 19/321
See application file for complete search history.

(56) References Cited

U.S. PATENT DOCUMENTS

| | | | | | |
|---|---|---|---|---|---|
| 5,987,345 | A | * | 11/1999 | Engelmann | ........... G06F 19/321 600/407 |
| 6,597,939 | B1 | * | 7/2003 | Lampotang | ............ A61B 6/541 128/202.13 |
| 2002/0133061 | A1 | * | 9/2002 | Manetta | ............... A61M 16/021 600/300 |
| 2008/0306766 | A1 | * | 12/2008 | Ozeki | ................... G06F 19/321 705/2 |

(Continued)

FOREIGN PATENT DOCUMENTS

| JP | 2007-159934 | 6/2007 |
|---|---|---|
| JP | 2007-233841 | 9/2007 |

(Continued)

OTHER PUBLICATIONS

Office Action dated Mar. 5, 2020 issued in Japanese Patent Application No. 2016-160944.

(Continued)

*Primary Examiner* — Nay A Maung
*Assistant Examiner* — Jose M Torres
(74) *Attorney, Agent, or Firm* — Cozen O'Connor (57) ABSTRACT

A radiographic-image processing apparatus includes an acquiring section configured to acquire not only data on each moving image but also an information item obtained in a predetermined time from capturing of the corresponding moving image if a plurality of moving images captured at different times is designated, and an allocating section configured to perform a process of saving each information item acquired by the acquiring section in a storage section in association with a data item on a corresponding moving image of the designated individual moving images.

6 Claims, 6 Drawing Sheets

(56) References Cited

U.S. PATENT DOCUMENTS

| | | | | |
|---|---|---|---|---|
| 2010/0246925 A1* | 9/2010 | Nagatsuka | ............... | A61B 5/08 382/132 |
| 2011/0311026 A1* | 12/2011 | Lalena | ................. | A61B 6/4405 378/98.5 |
| 2012/0054230 A1* | 3/2012 | Kanada | .................. | G16H 15/00 707/769 |
| 2013/0235080 A1* | 9/2013 | Robinson | ............ | A61M 1/3666 345/634 |
| 2013/0249702 A1* | 9/2013 | Terai | ...................... | A61B 5/743 340/691.6 |

FOREIGN PATENT DOCUMENTS

| | | |
|---|---|---|
| JP | 2009-100948 | 5/2009 |
| JP | 2010-172462 | 8/2010 |
| JP | 2014-236830 | 12/2014 |
| JP | 2015-196073 | 11/2015 |
| JP | 2016-071493 | 5/2016 |
| JP | 2016-073466 | 5/2016 |
| JP | 2016-087325 | 5/2016 |
| WO | WO 2014/168216 | 10/2014 |

OTHER PUBLICATIONS

Office Action dated Aug. 6, 2020 issued in Japanese Patent Application No. 2016-160944.
Office Action dated Oct. 30, 2020 issued in Japanese Patent Application No. 2016-160944.

\* cited by examiner

| | CAPTURED PART | CAPTURED FORM | CAPTURING DATE |
|---|---|---|---|
| ● | FRONT OF CHEST PART | MOTION | ○○○○/○○/○○ |
| ○ | FRONT OF CHEST PART | MOTION | ○○○○/○○/○○ |
| ○ | FRONT OF CHEST PART | MOTION | ○○○○/○○/○○ |

PATIENT : A

RADIOGRAPHIC-IMAGE PROCESSING APPARATUS

CROSS-REFERENCE TO RELATED APPLICATIONS

The entire disclosure of Japanese Patent Application No. 2016-160944 filed on Aug. 19, 2016 including description, claims, drawings, and abstract are incorporated herein by reference in its entirety.

BACKGROUND OF THE INVENTION

Field of the Invention

The present invention relates to a radiographic-image processing apparatus.

Description of the Related Art

In the related art, diagnoses have been performed based on still images by capturing the still images by radiographic imaging (x-ray imaging) on films, screens, or photostimulable phosphor plates. However, semiconductor image sensors such as a flat panel detector (FPD) comes to be used for capturing images of motions of diagnostic subject parts (hereinafter, referred to as subject parts), and the images of motions are applied to the diagnoses.

Specifically, the image of the subject part is captured over a plurality of times per second by consecutively emitting pulsed radiation from a radiation source according to timings of reading and erasing of a semiconductor image sensor, relying on quick response in reading and erasing image data of the semiconductor image sensor, whereby motion of the subject part is recorded. Then, the plurality of frame images acquired by the motion imaging is sequentially displayed on a screen, and a doctor can observe a series of movements of the subject part.

Figure 7:
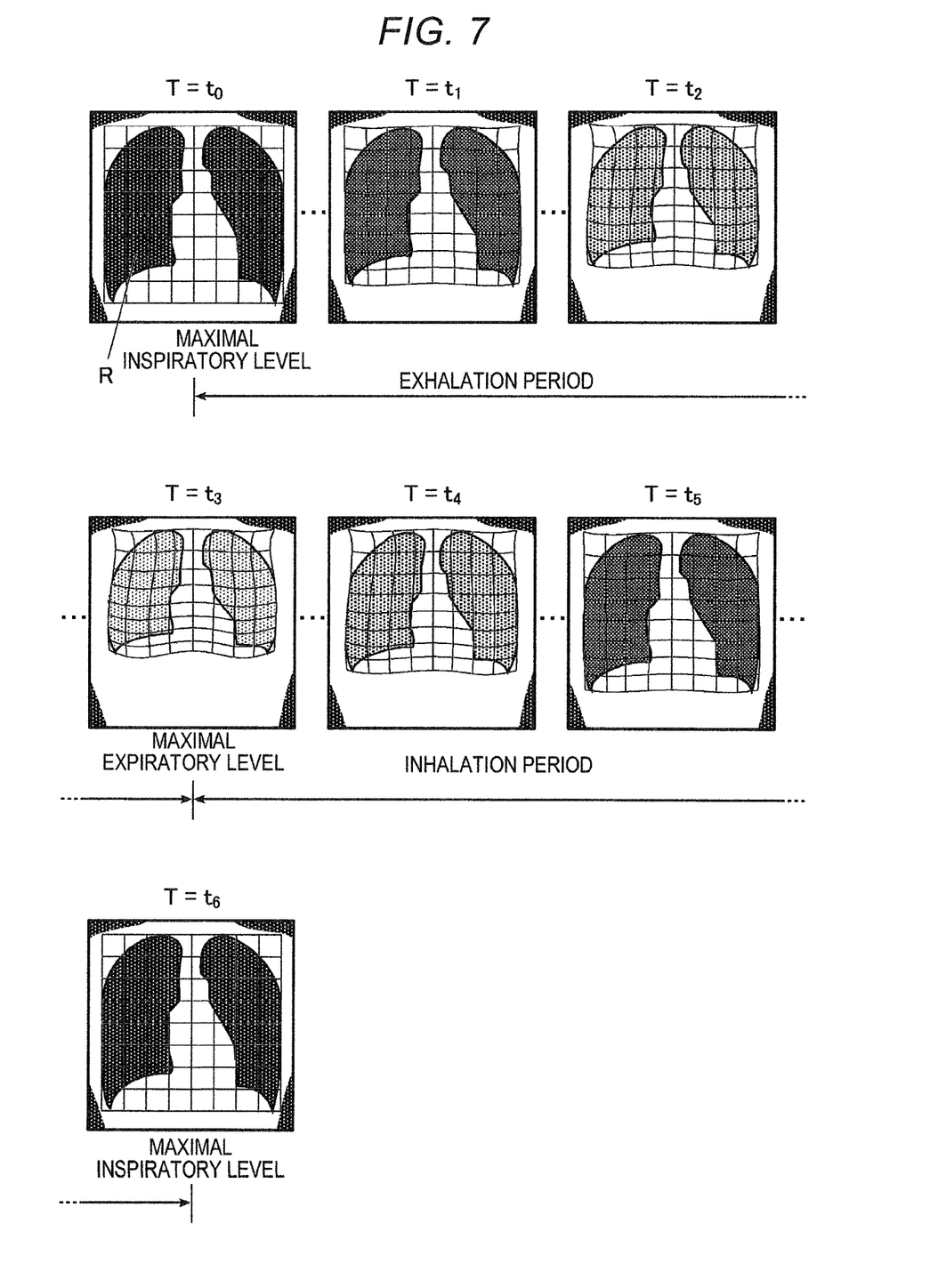
FIG. 7 is a view illustrating examples of moving images obtained by imaging motion of the chest part of a subject.

Further, for example, in a case where the subject part is lungs or a heart, the doctor can observe whether there is any part of the lungs of which functionality (such as a ventilatory function or a pulmonary blood stream function) has deteriorated or any part in which the heartbeat of the heart is abnormal so that the diagnosis can be performed by viewing the motion of the lungs or the heart reproduced on a screen, in other words, the individual frame images acquired by imaging the motion of the lungs or the heart (see FIG. 7 for instance).

Meanwhile, data on individual frame images captured by motion imaging as described above (broadly speaking, capturing of moving images) are acquired as electronic data, and thus can be stored in a storage section. Therefore, for example, with respect to a certain patient, a doctor can compare moving images captured by current motion imaging with past moving images obtained by motion imaging or the like in the past, thereby checking whether an abnormality found in the past has improved or worsened, or observing whether there is any new abnormal part, for performing the diagnosis.

In this regard, for example, JP 2015-196073 A discloses inventions on an X-ray imaging apparatus with which an operator such as a radiographer performs imaging. If the operator selects imaging order information, with respect to a patient who is a subject of current imaging, the X-ray imaging apparatus automatically acquires images of the patient captured in the past from an external system such as a picture archiving and communication system (PACS).

Also, JP 2007-233841 A discloses a system configured to display a list of object icons simply representing thumbnail images of images of a patient captured with each imaging apparatus such as a CR (computed radiography) apparatus, an ultrasonic diagnostic apparatus, an endoscopic apparatus, or a CT (computed tomography) scanner, and information like examination data of electrocardiogram examinations, blood examinations, physiological examinations, a medication history, and disease names, in a time line that is defined as horizontal axes. In this way, it is possible to grasp what imaging or examination was performed on the patient at what time in chronological order.

According to a configuration such that a plurality of moving images of a patient is captured at different times, the doctor may easily perform a diagnosis with reference to the displayed information, if the doctor can compare the individual moving images with information such as, information of examination data of examinations which is performed on the patient during capturing of each moving image, information on setting parameters set in medical devices attached to the patient during capturing of each moving image, or information on parameters set in imaging apparatuses used to capture the moving images. The information on setting parameters may be parameters set in the medical devices such as a ventilator, a heart-lung machine, an anaesthetic machine, and an infusion machine.

However, it is cumbersome for the doctor to search through various apparatuses, systems, and so on for obtaining the examination data of an examination performed in a timing when the moving image of the patient was captured (or at a timing close to the capturing timing), and allocate the searched examination data to the data on the corresponding moving image. It is likely to induce inappropriate diagnosis, by omitting some information that should be searched for, or by failing to allocate the examination data to the data on a moving image appropriately.

SUMMARY OF THE INVENTION

The present invention was made in view of the above-described problem, and an object of the present invention is to provide a radiographic-image processing apparatus capable of automatically and accurately collecting information items to be allocated to data items on a plurality of moving images captured at different times and be subjects to be compared by a doctor for making a diagnosis, and accurately allocating the collected information items to the data items on the moving images, respectively.

To achieve the abovementioned object, according to an aspect, a radiographic-image processing apparatus reflecting one aspect of the present invention comprises: an acquiring section configured to acquire an information item on a moving image by designating a plurality of the moving images, the moving image being each one of the plurality of the moving images captured at different times from one another, the information item being obtained in a predetermined time from a timing of capturing the corresponding moving image, the information item being other than information that is obtained based on the corresponding captured moving image; and an allocating section configured to perform a process of saving the information item, being acquired by the acquiring section, in a storage section in association with data corresponding to the moving image, the process of saving being performed for each one of the plurality of the moving images.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

Hereinafter, an embodiment of the present invention will be described with reference to the drawings. However, the scope of the invention is not limited to the illustrated examples.

In the following, an embodiment of a radiographic-image processing apparatus according to the present invention will be described with reference to the drawings.

Overall Configuration of Radiographic-Image Processing Apparatus

Figure 1:
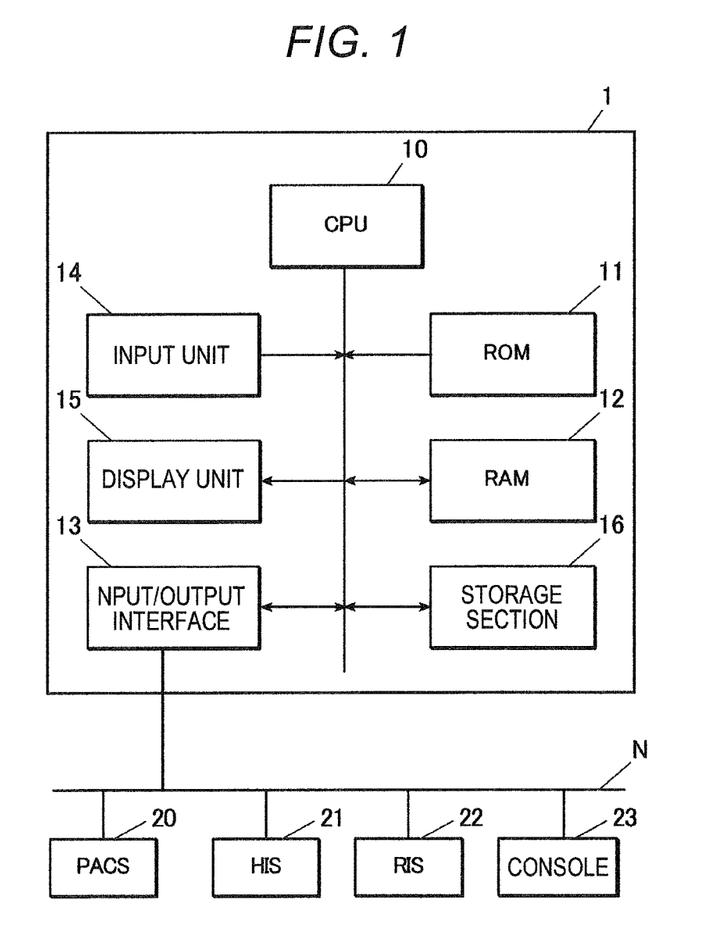
FIG. 1 is a block diagram illustrating an overall configuration of a radiographic-image processing apparatus according to an embodiment.

The overall configuration of a radiographic-image processing apparatus 1 according to the present embodiment will be described. FIG. 1 is a block diagram illustrating the overall configuration of the radiographic-image processing apparatus according to the present embodiment. According to the present embodiment, as shown in FIG. 1, the radiographic-image processing apparatus 1 is configured with a general-purpose computer including a central processing unit (CPU) 10, a read only memory (ROM) 11, a random access memory (RAM) 12, an input/output interface 13, and so on connected via a bus. Further, the radiographic-image processing apparatus is connected to a network N through the input/output interface 13.

Also, the CPU 10 is connected to other units such as an input unit 14 configured with a keyboard, a mouse, a touch panel, and so on, and a display unit 15 configured with a cathode ray tube (CRT), a liquid crystal display (LCD), or the like. Further, the CPU 10 is connected to a storage section 16 configured with a non-volatile semiconductor memory, a hard disk drive (HDD), and so on.

However, the radiographic-image processing apparatus 1 can be configured with a dedicated apparatus, not with the above-mentioned general-purpose computer. Also, for example, the display unit 15 may be configured with a display device or the like separate from the main body of the radiographic-image processing apparatus 1, and the present invention includes the case where the display unit 15 is configured with a device or the like separate from the main body and will be described as the radiographic-image processing apparatus 1.

Also, as shown in FIG. 1, according to the present embodiment, the radiographic-image processing apparatus 1 is connected to external systems such as a PACS 20, a hospital information system (HIS) 21, and a radiology information system (RIS) 22, a console 23 for controlling capturing of moving images in an imaging room, and so on, by the network N. Also, other necessary systems, devices, and so on can be appropriately connected to the network N.

The following description will be made on the assumption that data items on a plurality of moving images to be subjects are stored in advance in the storage section 16 of the radiographic-image processing apparatus 1. However, for example, the radiographic-image processing apparatus may be configured to acquire data items on moving images, and the like from an image storage database (not shown in the drawings), the PACS 20, the console 23, or the like retaining images, moving images, and so on captured, through the network N.

Also, according to the present embodiment, information on imaging parameters, such as a tube voltage, a tube current, an irradiation time (or milliamperes per second (mAs) per frame), and the sensitivity of an FPD, set in an imaging apparatus such as a radiation irradiation apparatus used to capture each moving image is stored in the PACS 20 in association with the generated moving image. However, such information may be stored in the console 23, a database (not shown in the drawings), or the like. Also, the radiographic-image processing apparatus 1 may be configured to acquire such information from the HIS 21, the RIS 22, or the like.

Also, in the present embodiment, information such as examination data on patients obtained by examination devices like a pulse oximeter and an electrocardiograph, and setting parameters set in medical devices like a ventilator attached to patients are stored in the HIS 21. However, a database (not shown in the drawings) for saving such information, a server for managing such information, and so on may be provided. Such information may be stored in a cloud storage server (not shown in the drawings). Also, examination devices and medical devices may be connected to the network N such that the radiographic-image processing apparatus 1 can directly acquire information such as examination data and the setting parameters from the examination devices and the medical devices.

Also, according to the present embodiment, the radiographic-image processing apparatus 1 is configured to be able to perform an image analysis process on moving images captured and use information such as feature data obtained by the image analysis process as examination data. Further, the information such as the feature data which is examination data is stored in the storage section 16 of the radiographic-image processing apparatus 1. Also, with saving of the information such as the feature data, analysis parameters (such as a low-frequency cutoff frequency of a lowpass filter) used to perform the image analysis process on the moving images are stored in the storage section 16 in association with the examination data.

Also, according to the present embodiment, besides examination data on a patent obtained by examination devices as described above, information such as feature data obtained by performing image analysis processes in other radiographic-image processing apparatuses, and information such as feature data obtained by performing image analysis processes in the past in the radiographic-image processing apparatus 1 can be used as examination data, and are stored in the PACS 20, the HIS 21 (or a database (not shown in the drawings)), or the like. Further, as described above, the information such as the feature data which is examination data is stored in the PACS 20, the HIS 21, or the like in association with analysis parameters used to perform image analysis processes on moving images.

Also, examples of feature data include feature data on a ventilatory function and a pulmonary blood stream function (i.e., an amplitude, a period, an absolute ventilation volume, an estimate ventilation volume, and so on) calculated by performing an image analysis process on moving images obtained by capturing a chest part of a subject including left and right lungs as shown in FIG. 7. With respect to a calculating method and the like of such feature data, for example, WO 2009/090894, JP 2009-273671 A, and JP 2009-153678 can be referred to.

Also, as feature data, a change in the concentration of a local area R (see FIG. 7) in a lung field, a change in the area of a lung field (the amount of motion of the contour of a lung field), the amount of movement of a diaphragm (the amount of motion of a diaphragm), the amount of movement of an external thorax (the amount of motion of an external thorax), a speed relative to change in the concentration of a lung field, a speed relative to change in the area of a lung field, a speed relative to motion of a diaphragm, a speed relative to motion of an external thorax, pulmonary compliance (an index indicating lung's pliableness), a change in the concentration of a heart area, a change in the wall of a heart (the amount of motion of the contour of the wall of a heart), and so on can be used. Further, as feature data, besides the above-mentioned data items, appropriate data items may be calculated.

With Respect to Information Acquisition and Association of Information to Data on Moving Images According to the present embodiment, the CPU 10 of the radiographic-image processing apparatus 1 is configured to function as an acquiring section and an allocating section of the present invention (to be described below). Therefore, in a case where the CPU 10 functions as the acquiring section or the allocating section, the CPU will be referred to as the acquiring section 10 or the allocating section 10.

Figure 2:
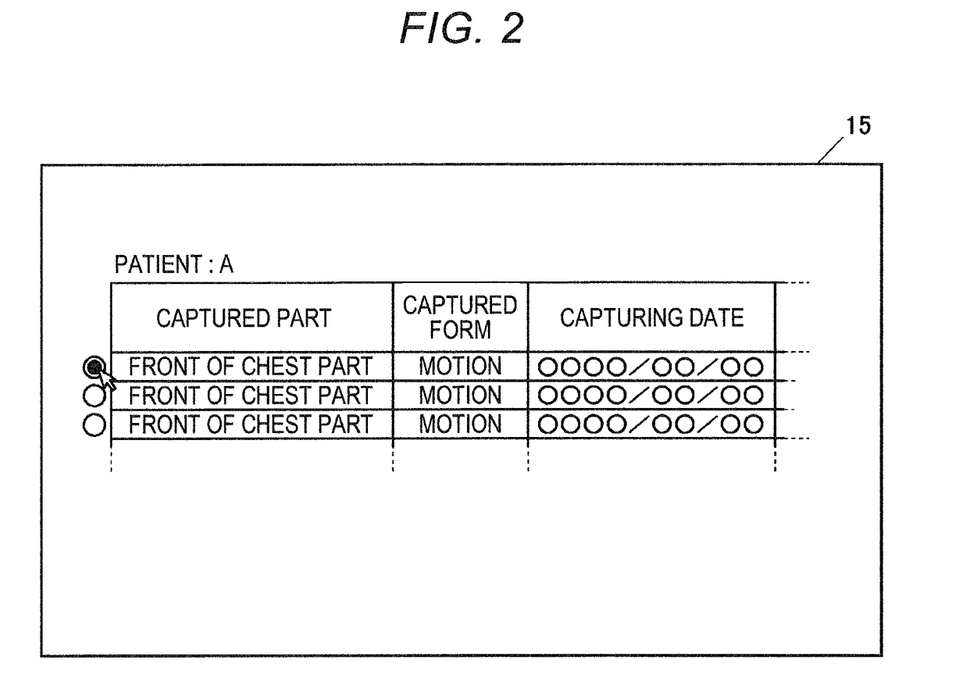
FIG. 2 is a view illustrating an example of a list of imaging records on a patient displayed on a display unit.

The acquiring section 10 is configured such that if a user such as a doctor designates a plurality of moving images P1, P2, . . . of the same subject part (such as the front of a chest part) of a patient A captured at different times t1, t2, . . . , for example, by selecting them from a list of imaging records on the patient A displayed on the display unit 15 as shown in FIG. 2, the acquiring section acquires information p on each of the plurality of moving images P1, P2, . . . obtained in a predetermined time from capturing of the corresponding moving image, for example, by searching the storage section 16 included in the radiographic-image processing apparatus, and the PACS 20, the HIS 21, the RIS 22, the console 23, and soon connected to the radiographic-image processing apparatus by the network N.

In the following, a case where the acquiring section 10 is configured to perform a process of acquiring data on necessary moving images P and necessary information p when the user such as a doctor has completed selection (i.e., during radiogram interpretation of the doctor) will be described. However, the acquiring section 10 may be configured to perform an acquiring process of acquiring data on moving images P and information p having not been acquired, regularly (or at predetermined timings). Alternatively, the acquiring section may be configured to perform an acquiring process if a moving image is captured (or before capturing of a moving image).

In the present embodiment, information p which is acquired as described above includes examination data pc on patients (including feature data obtained by performing image analysis processes as described above), setting parameters ps of medical devices such as a ventilator attached to patients, imaging parameters px set imaging apparatuses used to capture moving images, and so on. Also, information p may include analysis parameters pa used to perform image analysis processes on moving images.

In this case, the acquiring section 10 acquires the information p obtained in the predetermined time from capturing of each of the designated moving images P. In this case, the predetermined time is determined for each item of the information p.

Meanwhile, in a case of performing the same examination on a patient with an examination device such as a pulse oximeter, an electrocardiograph, a vital monitor of body temperature, respiration rate, heart rate, pulse rate, and so on, a capnometer, an invasive sphygmomanometer, or a urine volume meter to obtain examination data pc, the examination may be performed at the same time as capturing of a moving image, or the examination may be performed in real time just after capturing of a moving image (in this case, the predetermined time is 0). However, sometimes, the examination is performed before and after capturing of a moving image. For this reason, some types of examinations can be performed immediately, and some types of examinations cannot be performed immediately.

For this reason, with respect to examination data pc which is obtained by performing examinations on patients with examination devices as described above, a time is determined depending on the type of the examination in advance. For example, with respect to a comparatively easy examination which can be performed with an examination device such as a pulse oximeter or an electrocardiograph, several minutes to ten minutes from capturing of a designated moving image P is determined. Also, for example, with respect to each of an examination requiring a relatively long time like a blood chemistry examination, a gas analysis examination which is performed on a blood sample taken from an artery and requires a long time to prepare the examination, an examination like esophageal pressure (pleural pressure) measurement using an examination device such as a catheter, 10 minutes to 30 minutes before and after capturing of a designated moving image P is determined.

Further, in this case, the acquiring section 10 has, for example, information representing the relation between examination types and predetermined times, for example, in the form of a table, although the corresponding information is not shown in the drawings, and is configured to acquire examination data obtained by an examination performed in a predetermined time before and after capturing of a moving image P, as the examination data pc, if the corresponding moving image P is designated by the user such as a doctor.

Also, even in a case of attaching medical devices to patients or changing setting parameters ps of medical devices, some medical devices can be attached in the midst of capturing of a moving image, or some medical devices cannot be attached in the midst of capturing of a moving image, and thus are attached before or after capturing of a moving image. For this reason, even with respect to setting parameters ps of medical devices, a time is determined in advance for each medical device. For example, for a ventilator, several minutes to 10 minutes before and after capturing of a designated moving image P is determined in advance.

Further, even in this case, the acquiring section 10 has, for example, information representing the relation between medical devices and predetermined times, for example, in the form of a table, although the corresponding information is not shown in the drawings, and is configured to acquire setting parameters ps set in a medical device attached to the patient in a predetermined time before or after capturing of a moving image P, if the corresponding moving image P is designated by the user such as a doctor.

According to the present embodiment, if a plurality of moving images captured at different times is designated by the user such as a doctor as described above, the acquiring section 10 acquires an information item p on each moving image, i.e., examination data pc (such as feature data), setting parameters ps, imaging parameters px, and the like. Then, the allocating section 10 performs a process of saving each information item p in the storage section 16 in association with a data item on a corresponding moving image P of the designated moving images P1, P2, . . . . As an allocating method, for example, a method of writing information p in the header of data on each moving image P is performed.

With Respect to Process Which is Performed in Case Where it is Impossible to Acquire Examination Data pc Such as Feature Data For example, in a case where some or all of the plurality of designated moving images P1, P2, . . . have been captured but have not been yet subjected to an image analysis process, or a case where all of the moving images have been captured but some or all of the examination data pc have not been yet subjected to an image analysis process, the acquiring section 10 cannot acquire the examination data pc such as the feature data. However, in this case, even though it is impossible to acquire the examination data pc such as the feature data, it is possible to calculate the necessary examination data pc by performing an image analysis process on the moving images P.

Therefore, in the present embodiment, in a case where some necessary examination data pc such as feature data has not been calculated with respect to the plurality of moving images P1, P2, . . . captured at different times t1, t2, . . . , the allocating section 10 performs an image analysis process on some or all of the moving images, thereby calculating the analysis result as examination data pc, and saving the examination data in the storage section 16 in association with the moving images P subjected to the image analysis process.

According to this configuration, even in a case where necessary examination data pc such as the feature data has not been calculated with respect to some designated moving images P, if there are those moving images P, it is possible to calculate necessary examination data pc by performing an image analysis process on the moving images, and it is possible to accurately allocate the examination data to the moving images P subjected to the image analysis process.

Effects

As described above, according to the radiographic-image processing apparatus 1 of the present embodiment, if the plurality of moving images P1, P2, . . . captured at the different times t1, t2, . . . is designated by the used such as a doctor, with respect to each of the moving images P1, P2, . . . , the acquiring section 10 automatically acquires an information item such as examination data pc (including the feature data and the like) obtained in a predetermined time from capturing, setting parameters ps, and imaging parameters px. Then, the allocating section 10 automatically performs a process of saving each information item p acquired by the acquiring section 10 in the storage section 16 in association with a data item on corresponding moving images P of the designated moving images P1, P2, . . . .

Therefore, it is possible to automatically and accurately collect information items p (such as examination data pc, setting parameters ps, and imaging parameters px) to be allocated to data items on the plurality of moving images P1, P2, . . . captured at the different times t1, t2, . . . and be subjects to be compared by a doctor for making a diagnosis, and accurately allocate the collected information items to the data items on the moving images P1, P2, . . . , respectively.

Therefore, the user such as a doctor needs only to designate the plurality of moving images P1, P2, . . . , and thus can very easily allocate the information items p to the data items on the moving images P1, P2, . . . , respectively. Also, it is possible to collect and acquire the necessary information items p without omissions, and it is possible to surely prevent errors in allocating the information items p such as the examination data pc to the data items on the moving images P1, P2, . . . , respectively. Therefore, a doctor can appropriately make a diagnosis.

With Respect to Display of Plurality of Moving Images on Display Unit

Now, a case where the radiographic-image processing apparatus 1 according to the present embodiment displays the moving images P1, P2, . . . associated with the information p acquired in the above-mentioned way on the display unit 15 will be described.

In the following, a case where two moving images P1 and P2 captured at the different times t1 and t2 are designated and displayed will be described. However, the same configuration can be applied even in a case where three or more moving images P are displayed. Also, in the present embodiment, the CPU 10 of the radiographic-image processing apparatus 1 is configured to function as a display control section of the present invention (to be described below). Further, in a case where the CPU 10 functions as the display control section, the CPU will be referred to as the display control section 10.

Figure 3:
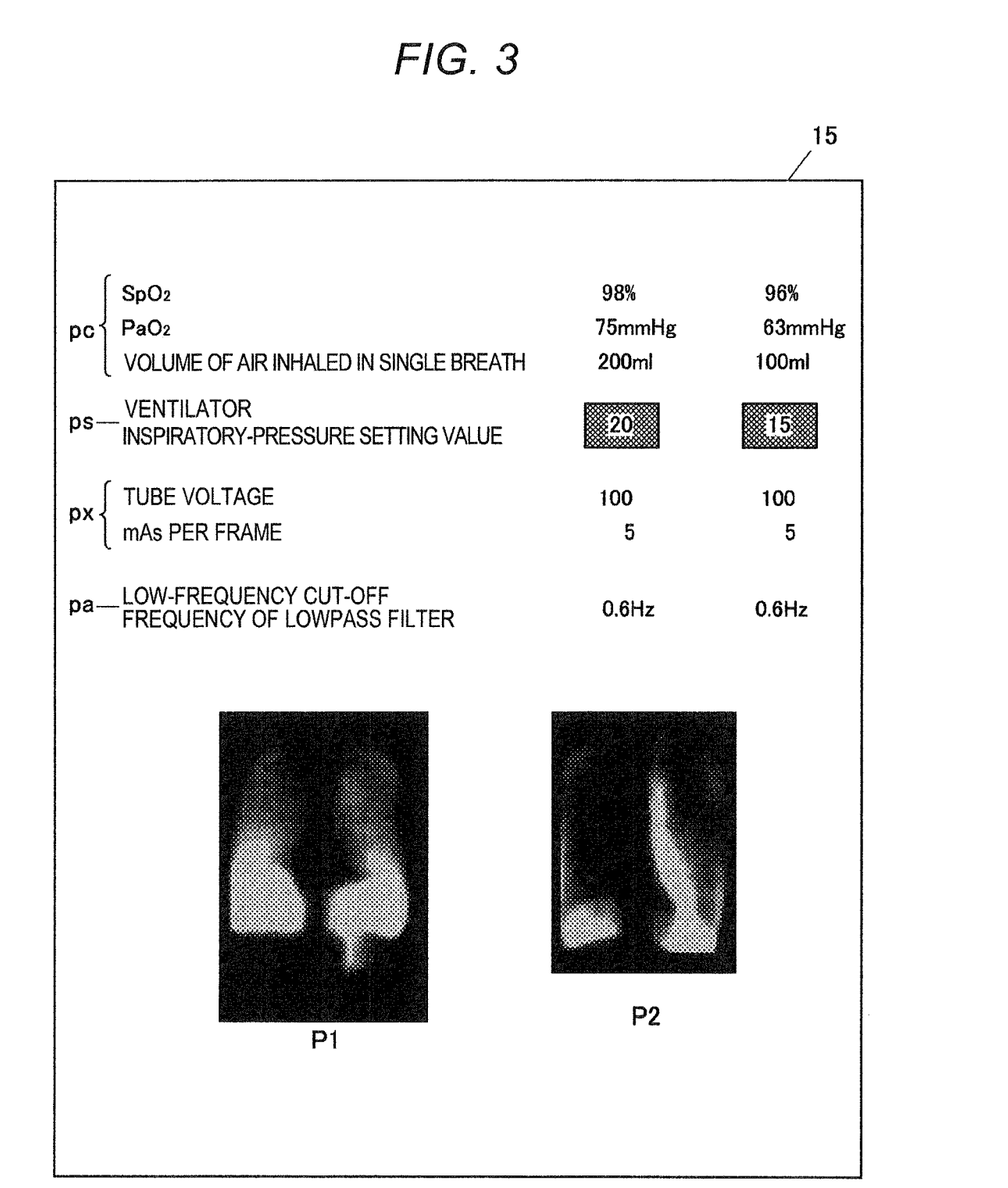
FIG. 3 is a view illustrating a plurality of moving images, acquired information, and so on displayed in the same screen of the display unit.

In the present embodiment, as shown in FIG. 3, the plurality of moving images P1 and P2 captured at the different times t1 and t2 are displayed on the display unit 15. At this time, the display control section 10 performs control such that acquired information items p are displayed on the same screen in association with the moving images P1 and P2 to which the corresponding information items p have been allocated, respectively.

The example of FIG. 3 shows a case where, in association with each of the moving images P1 and P2, $SpO_2$ which is an output value of a pulse oximeter, $PaO_2$ which is a result of arterial blood gas analysis examination, the volume of air inhaled in a single breath which is an output value of a ventilator, and the like are displayed as examination data pc (including feature data and the like), and an inspiratory-pressure setting value of the ventilator is displayed as a setting parameter ps, and a tube voltage and milliamperes per second (mAs) per frame are displayed as imaging parameters px. Also, $SpO_2$ means the level of blood oxygen saturation, and represents the ratio of oxygenated hemoglobin in blood. Also, $PaO_2$ means arterial oxygen pressure, and is the index of lung's blood oxygenation capability (the amount of oxygen in blood). Further, as shown in FIG. 3, in association with each of the moving images P1 and P2, a low-frequency cut-off frequency of a lowpass filter may be displayed as an analysis parameter pa.

According to this configuration, when a doctor views the plurality of moving images P1 and P2, the doctor can see the information p obtained at the times t1 and t2 when the moving images P1 and P2 were captured (or at times close to the times t1 and t2), i.e., the examination data pc (including the feature data and the like), the setting parameters ps, the imaging parameters px, and the like, on the same screen. Further, it is possible to display the information p more visibly and perspicuously. Therefore, the doctor can easily and accurately make a diagnosis by viewing the displayed information.

Also, since the moving images P1 and P2 and the information p corresponding to those moving images are displayed on the same screen, the doctor can accurately observe change of the subject part (in this case, lungs, a heart, or the like) of the patient with time.

In this case, if an information item of the information p to be displayed in association with the moving image P1 captured at the time t1 is different from a corresponding information item of the information p to be displayed in association with the moving image P2 captured at the time t2, the display control section 10 may perform control such that the corresponding information items p are highlighted on the display unit 15.

Specifically, for example, in a case where an information item p obtained during capturing of the moving image P1 is different from a corresponding information item p obtained during the moving image P2, it is possible to highlight the display fields of the corresponding information items in a color (for example, yellow) different from the color (for example, white) of the other fields (see display fields of setting parameters ps of FIG. 3, i.e., display fields of inspiratory-pressure setting values "20" and "15" of the ventilator, for instance).

Alternatively, only the information items p different from each other may be highlighted in a color different from the color of the other information p. For example, in the example of FIG. 3, since the information items "$SpO_2$", "$PaO_2$", and "VOLUME OF AIR INHALED IN SINGLE BREATH" which are the examination data pc of the moving image P1 are different from those of the moving image P2, those information items may be highlighted, for example, in red (in this case, the other numerical values may be displayed, for example, in black).

According to this configuration, in a case where any information item p obtained during capturing of the moving image P1 is different from a corresponding information item obtained during capturing of the moving image P2, it is possible to display those information items such that a doctor can accurately recognize them. Further, for example, in the case of FIG. 3, if a doctor views the display of the screen, the doctor can grasp that if the inspiratory-pressure setting value of the ventilator changes (from 20 to 15), the ventilation volume of the lung field degrades (from 200 ml to 100 ml), and accurately determine that it is preferable to restore the inspiratory-pressure setting value of the ventilator (from 15 to 20).

As described above, according to the above-described configuration, doctors and the like can appropriately determine whether the setting of a medical device was proper (with respect to setting parameters ps), whether the setting of an imaging device was proper (with respect to imaging parameters px), and the like, and set more appropriate parameters. Also, according to the configuration in which analysis parameters pa are displayed in association with the moving images P1 and P2, respectively, as shown in FIG. 3, doctors and the like can appropriately determine whether an image analysis process has been performed on each moving image, and set more appropriate parameters.

Also, thresholds may be set for the types of the information items p, respectively, and in a case where a change in an information item exceeds a set threshold, the corresponding information item may be highlighted. According to this configuration, doctors and the like can easily grasp significantly changed information items p which should be checked. Also, in a case where an imaging parameter px has changed, the change of the imaging parameter may be compensated by correcting the results of the image analysis process on the moving images, or by performing a correcting process on the moving images and then performing an image analysis process. For example, if the tube voltage of the moving image P2 is higher than that of the moving image P1, since the image contrast between the images, i.e., the concentration change is small due to the difference between the tube voltages, the concentration change in a local area of the lung field obtained as a result of the image analysis process on the moving image P2 is corrected by multiplying the result by a coefficient larger than 1. Also, for example, if the moving image P2 was captured in a state where an FPD had sensitivity which was two thirds of that of the moving image P1, the moving image P2 is corrected by multiplying the values of the individual pixels by 1.5, and then an image analysis process is performed. According to this configuration, doctors and the like can check image analysis process results compensated in the differences in imaging parameters, and easily understand a chronological change or difference.

Figure 4:
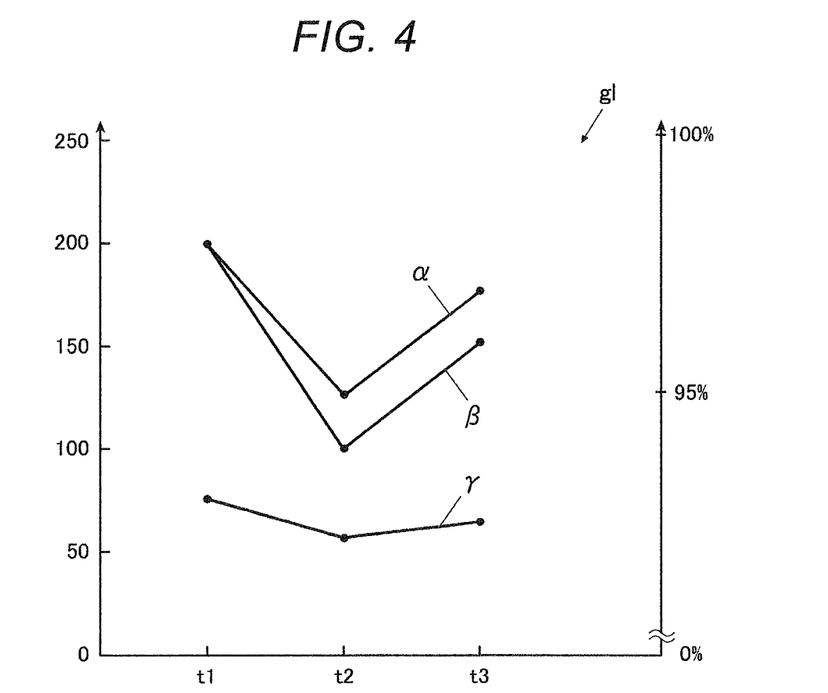
FIG. 4 is a graph illustrating an example of change of information with time.

Meanwhile, the display control section 10 can be configured to perform control such that a graph g1 representing the chronological change of the above-mentioned information items p (including the analysis result which the allocating section 10 calculated by performing the image analysis process on the moving images P, i.e., the examination data pc such as the feature data) is displayed on the display unit 15 as shown in FIG. 4.

Also, FIG. 4 shows the graph g1 representing, for example, the chronological change of information items p (the examination data pc) such as "$SpO_2$" (see a reference symbol "$\alpha$" in FIG. 4), "$PaO_2$" (see a reference symbol "$\beta$" in FIG. 4), and "VOLUME OF AIR INHALED IN SINGLE BREATH" (see a reference symbol "$\gamma$" in FIG. 4). Further, according to this configuration, it is possible to check how each information item of the information p changes chronologically by viewing the graph g1.

Also, the display control section 10 can be configured to perform control such that a graph g2 representing the relation between the information p and the analysis result calculated by performing the image analysis process on the moving images P, i.e., the examination data pc such as the feature data is displayed on the display unit 15.

For example, A-$aDO_2$ (the alveolar-arterial oxygen difference) which is a result of the arterial blood gas analysis examination is taken as an example of the examination data pc. A-$aDO_2$ is the index of alveolar gas exchange, and is a measurement value which can be calculated from $PaO_2$ and $PaCO_2$ (arterial carbon dioxide pressure) measured like $PaO_2$ by arterial blood gas analysis, and has a large value in type 1 respiratory failure (gas exchange failure).

Also, for example, by performing the image analysis process on the moving images P, it is possible to calculate the degree of ventilation-perfusion ratio inequality of the lungs as the analysis result, for example, as an index of gas exchange failure of the lungs. Further, this is taken as an example of the above-mentioned information p (i.e., the examination data pc such as the feature data). With respect to the degree of ventilation-perfusion ratio inequality, for example, concentration change components of a breathing cycle and concentration change components of a cardiac cycle are calculated as concentration changes of ventilation and concentration changes of the stream of blood, respectively, from the concentration changes in local areas of the lung field by a frequency filter of a time axis direction, whereby the concentration changes of ventilation and the bloodstream in each local area of the lung field are calculated, respectively. Then, it is possible to obtain images representing the distributions of the concentration changes of ventilation and the bloodstream in the lung field. Therefore, it is possible to calculate the degree of ventilation-perfusion ratio inequality by standardizing the distribution images of ventilation and the bloodstream such that it is possible to easily compare the images, for example, by dividing the values of the individual local areas by the average value of the lung field, and calculating the dissimilarity between the distribution images of ventilation and the bloodstream, for example, by calculating the sum of the squares of the differences of the individual local areas between both images, or the sum of the absolute values of the differences.

Also, $A\text{-}aDO_2$ which is the index of gas exchange failure in the arterial blood gas analysis examination is calculated as the examination data pc by capturing a moving image of the lungs (see FIG. 7) while performing arterial blood gas analysis examination, and the degree of ventilation-perfusion ratio inequality of the lungs is calculated as the information p by performing an image analysis process on the moving image. This is performed a plurality of times. Then, by performing plotting using a horizontal axis and a vertical axis representing the information p (in the above-described case, the degree of ventilation-perfusion ratio inequality of the lungs) and the examination data pc (in the above-described case, $A\text{-}aDO_2$ obtained in the arterial blood gas analysis examination), respectively, for example, the graph g2 as shown in FIG. 5 is obtained.

Therefore, according to this configuration in which the graph g2 is displayed on the display unit 15, it is possible to clearly recognize the relation between the information p and the examination data pc (for example, the relation between the degree of ventilation-perfusion ratio inequality of the lungs and $A\text{-}aDO_2$ which is the index of gas exchange failure).

With Respect to Estimation of Examination Data pc and Setting Parameters ps Based on Analysis Result (Information p)

Figure 5:
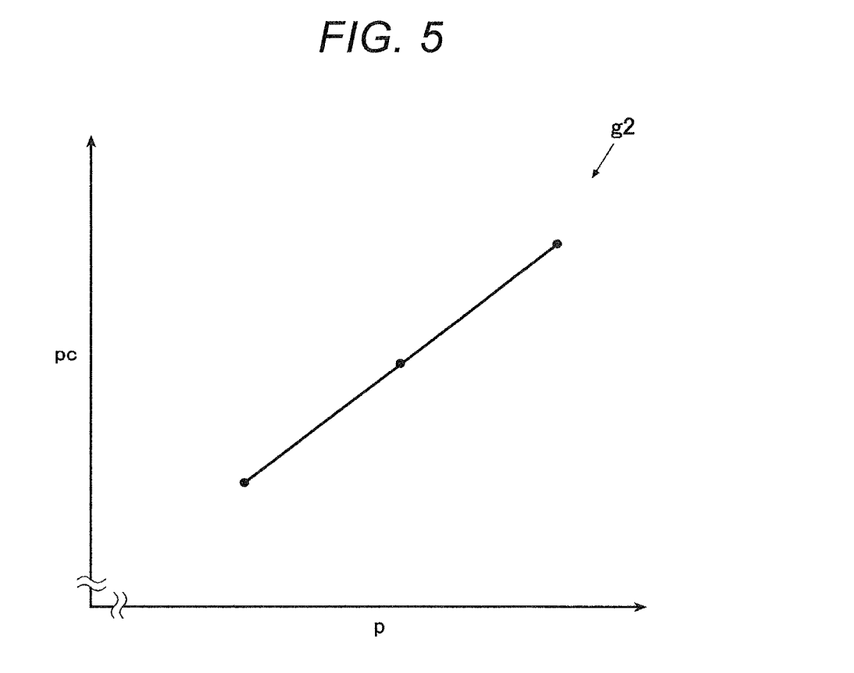
FIG. 5 is a graph having a horizontal axis representing information (the degree of ventilation-perfusion ratio inequality of lungs) and a vertical axis representing examination data (A-aDO$_2$ obtained by an arterial blood gas analysis examination)

Meanwhile, for example, if the relation as shown in FIG. 5 is known, it is possible to estimate the examination data pc (in the case of FIG. 5, $A\text{-}aDO_2$ which is the gas exchange failure index obtained by the arterial blood gas analysis examination), for example, based on the information p (in the case of FIG. 5, the degree of ventilation-perfusion ratio inequality of the lungs) obtained by performing the image analysis process on the moving images.

To this end, the radiographic-image processing apparatus 1 according to the present embodiment may be configured to have an estimating section for calculating estimate values pe of the examination data pc of a patient based on an analysis result p, i.e., the above-mentioned information p calculated by performing the image analysis process on the moving images P. For example, the CPU 10 of the radiographic-image processing apparatus 1 can be configured to function as the estimating section.

For example, since the arterial blood gas analysis examination is highly invasive to patients, and it is painful for patients to frequently take blood samples from an artery by arterial puncture using injections, and even in continuously taking a blood sample from an artery for a long time through a catheter inserted into the artery, there is the risk of infection, thrombi, and emboli, it is impossible to perform moving-image capturing while performing the arterial blood gas analysis examination whenever moving-image capturing (motion capturing) as shown in FIG. 7 is performed, and thus sometimes, only moving-image capturing should be performed without performing arterial blood gas analysis examination.

Therefore, in this case, if it is possible to estimate $A\text{-}aDO_2$ which is the index of gas exchange failure in the lung field which would be measured in a case of performing the arterial blood gas analysis examination at the same time as moving-image capturing, based on the above-described information p (particularly, the examination data pc such as the feature data) obtained by performing image processing on moving images acquired by moving-image capturing, it may be helpful for doctor's diagnosing.

Therefore, in the above-described configuration, for example, if it is possible to obtain the relation (the graph g2) as shown in FIG. 5 in advance and use the obtained relation to calculate the estimate values pe of the examination data pc of the patient based on the analysis result p, i.e., the above-described information p calculated by performing the image analysis process on the moving images P, for example, by regression expressions, interpolation, and extrapolation, even in a case where it is impossible to obtain the examination data pc of the patient (for example, $A\text{-}aDO_2$ which is obtained by arterial blood gas analysis examination), it is possible to appropriately calculate the estimate values pe of the examination data.

Also, even in a case where it is impossible to perform the arterial blood gas analysis examination and the like, it is possible to appropriately estimate the value of $A\text{-}aDO_2$ (i.e., the examination data pc) which would be obtained in a case of performing the arterial blood gas analysis examination. Therefore, even in this case, doctors can accurately make a diagnosis based on the estimate values pe, similarly in the case where the arterial blood gas analysis examination has been performed.

Also, in a case where the calculated estimate values pe are displayed together with the other information p on the same screen as that of the moving images P, for example, as shown in FIG. 3, if the estimate values pe are simply displayed, it may be impossible to recognize whether the displayed values are the information p actually measured or calculated or the estimate values pe. For this reason, when the estimate values pe are displayed, for example, a text "estimate" may be displayed before or after the numerical values such that it is possible to recognize that the displayed values are the estimate values pe.

Also, the above-described relation (the graph g2) is established not only between the analysis result p calculated by performing the image analysis process on the moving images P, i.e., the information p and the examination data pc of the patient (for example, A-aDO$_2$ obtained by the arterial blood gas analysis examination), but also, for example, between the information p and the setting parameters ps of the medical device such as a ventilator attached to the patient.

To this end, the estimating section may be configured to obtain the relation (not shown in the drawings) between the analysis result p, that is, the information p calculated by performing the image analysis process on the moving images P and the setting parameters ps of the medical device, in advance, and use the obtained relation to calculate the estimate values pe of the setting parameters ps set in the medical device based on the analysis result p (i.e., the information p) calculated by performing the image analysis process on the moving images P as if the medical device was attached to the patient although the medical device was not attached to the patient.

According to this configuration, even in a case where it is impossible to attach the medical device to the patient, doctors can accurately make a diagnosis based on the estimate values pe as if the medical device was attached to the patient.

With Respect to Moving-Image Capturing Situation and So On

Figure 6:
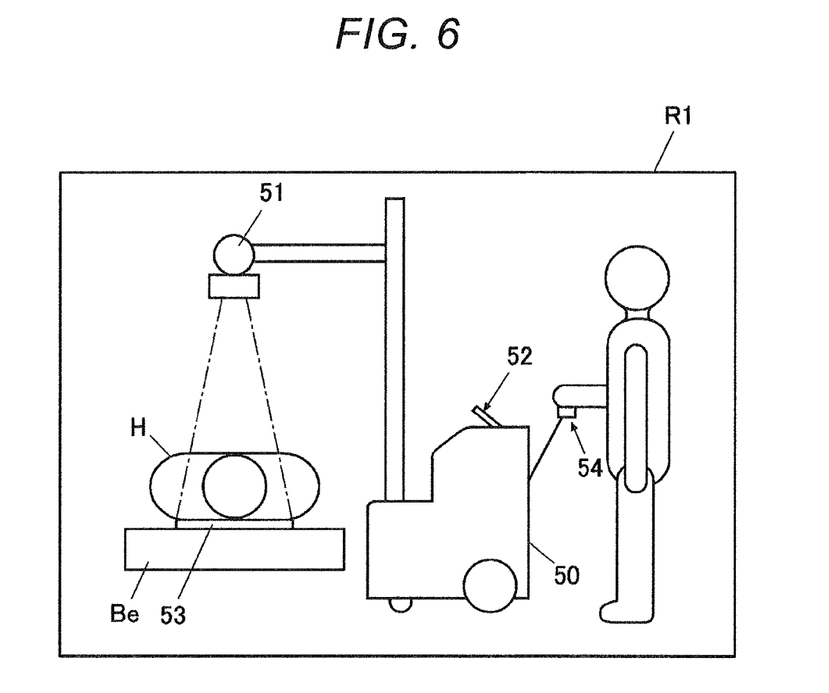
FIG. 6 is a view illustrating a state where imaging is performed with a round-visit cart equipped with a portable radiation irradiation apparatus, a console, and so on in an operating room or an intensive care unit.

Also, some or all of the plurality of moving images P1, P2, . . . captured at the different times t1, t2, . . . as described above may be moving images captured in an imaging room having a radiographic-image acquiring apparatus and a radiation irradiation apparatus (an installation type), and so on (not shown in the drawings). Alternatively, some or all of the plurality of moving images P1, P2, . . . may be moving images captured with a round-visit cart 50 equipped with a portable radiation irradiation apparatus 51 which is an imaging apparatus, a console 52, and so on, in an operating room, an intensive care unit (ICU) R1, or the like, for example, as shown in FIG. 6.

In this case, for example, a portable radiographic-image acquiring apparatus 53 is put between the body of the patient which is a subject H and the bed or on the body of the patient, and an operator like a radiographer operates an exposure switch 54 of the radiation irradiation apparatus 51, whereby the subject H is irradiated with radiation from the radiation irradiation apparatus 51, and imaging is performed. Also, in this case, although not shown in the drawings, sometimes, imaging is performed in a state where a drain, a catheter, a ventilator, or the like is attached to the patient.

A doctor or the like grasps the state (such as motion) of the subject part (for example, lungs or a heart) of the patient by viewing the moving images of the subject part captured by performing imaging in the above-described situation. However, at this time, for example, if the doctor is performing an operation or is treating a patient, even if the doctor wants to perform comparison with moving images of the same subject part captured in the past, the doctor cannot prepare moving images and information p such as examination data pc obtained in the past by himself.

However, according to the radiographic-image processing apparatus 1 of the present embodiment, for example, if a doctor or the like selects a current moving image P and a past moving image P from the list of imaging records on the corresponding patient as shown in FIG. 2, the radiographic-image processing apparatus 1 automatically acquires not only the current moving image P and all information p obtained in a predetermined time from capturing of the current moving image P, but also the selected past moving image P and all information p obtained in a predetermined time from capturing of the past moving image P, and displays them on the display unit 15.

Also, with respect to some information p which cannot be acquired but can be estimated, the above-described estimating process is performed, and estimate values pe are displayed on the display unit 15. Whenever an information item p is acquired or an estimate value pe is acquired, the radiographic-image processing apparatus 1 displays the acquired information item or the acquired estimate value on the display unit 15 in succession. Therefore, the plurality of moving images P and the necessary information p (including the estimate values pe) are displayed on the display unit 15 in a short time.

Therefore, even in a situation where a doctor cannot prepare (acquire) the past moving images and the information p such as the examination data pc by himself since he is performing an operation or is treating a patient, if the radiographic-image processing apparatus 1 according to the present embodiment is used, the apparatus automatically acquires the data on necessary moving images P and necessary information p, and in a case where there is not some necessary information p, if there is estimable information p, the apparatus automatically estimates and calculates the estimate values pe of the corresponding information.

Therefore, even in the above-mentioned situation, the doctor can compare the plurality of moving images P1, P2, . . . and the information p displayed on the display unit 15, thereby accurately determining the current state of the patient, and accurately performing an operation, a treatment, and the like on the patient. Further, in such a case where the doctor is tied up, the effect of the radiographic-image processing apparatus 1 of this application capable of automatically acquiring data on necessary moving images P and necessary information p exhibits beneficially.

Also, it goes without saying that the present invention is not limited to the embodiment and the like described above and can be appropriately modified without departing from the scope of the present invention.

According to an embodiment, a radiographic-image processing apparatus can automatically and accurately collect information items to be allocated to data items on a plurality of moving images captured at different times and be subjects to be compared by a doctor for making a diagnosis, and accurately allocate the collected information items to the data items on the moving images, respectively.

Although the present invention has been described and illustrated in detail, it is clearly understood that the same is by way of illustrated and example only and is not to be taken by way of limitation, the scope of the present invention being interpreted by terms of the appended claims.

What is claimed is:

1. A radiographic-image processing apparatus comprising:
   an acquiring section configured to acquire an information item on a moving image by designating a plurality of the moving images, the moving image being each one of the plurality of the moving images captured at different times from one another, the information item being obtained in a predetermined time before and after capturing the corresponding moving image, the information item comprising a setting parameter of a medical device attached to the patient;
   an allocating section configured to perform a process of saving the information item, being acquired by the acquiring section, in a storage section in association with data corresponding to the moving image, the process of saving being performed for each one of the plurality of the moving images;
a display unit configured to display the plurality of moving images captured at the different times; and
a display control section configured to perform control such that, when the plurality of moving images is displayed on the display unit, the acquired information item is displayed on same screen in association with the moving images to which the acquired information item has been allocated,
wherein:
when the information item is displayed in association with the plurality of moving images captured at the different times, if some setting parameters of a medical device attached to the patient information items corresponding to each other are different from each other, the display control section performs control such that the corresponding setting parameters of a medical device attached to the patient information items are highlighted on the display unit.

2. The radiographic-image processing apparatus according to claim 1, wherein:
the display control section performs control such that a graph representing chronological change of the information items is displayed on the display unit.

3. The radiographic-image processing apparatus according to claim 1, wherein:
the display control section performs control such that the relation between the information item and analysis data calculated by performing an image analysis process on the plurality of moving images captured at different times is displayed on the display unit.

4. The radiographic-image processing apparatus according to claim 1, further comprising:
an estimating section configured to calculate an estimate value of at least one of examination data of the patient and the setting parameter of the medical device attached to the patient, based on an analysis result calculated by performing an image analysis process on the plurality of moving images captured at different times.

5. The radiographic-image processing apparatus according to claim 1, wherein:
some or all of the plurality of moving images captured at the different times are moving images captured with an imaging apparatus mounted on a round-visit cart.

6. The radiographic-image processing apparatus according to claim 1, wherein the predetermined time is determined for each said information item.

* * * * *